United States Patent [19]

Kelly et al.

[11] Patent Number: 5,391,489

[45] Date of Patent: Feb. 21, 1995

[54] PROTEOLYTIC ENZYMES FROM HYPERTHERMOPHILIC BACTERIA AND PROCESSES FOR THEIR PRODUCTION

[75] Inventors: Robert M. Kelly, Ellicott City, Md.; Anne K. S. Robinson, Philadelphia, Pa.; Ilse I. Blumentals, Silver Spring, Md.; Stephen H. Brown, Owings Mills, Md.; Christian B. Anfinsen, Baltimore, Md.

[73] Assignee: Johns Hopkins University, Baltimore, Md.

[21] Appl. No.: 83,536

[22] Filed: Jun. 30, 1993

Related U.S. Application Data

[62] Division of Ser. No. 406,327, Sep. 12, 1989, Pat. No. 5,242,817.

[51] Int. Cl.$^6$ .................... C12P 21/04; C12N 9/52; C12N 9/50
[52] U.S. Cl. ........................ 435/220; 435/71.2; 435/212; 435/252.1; 435/219
[58] Field of Search ............... 435/71.2, 220, 219, 435/252.1, 212

[56] References Cited

U.S. PATENT DOCUMENTS 5,242,817  9/1993  Kelly et al. .................... 435/220

OTHER PUBLICATIONS

Khoo et al Biochem J. (1984) vol. 221 pp. 407–413.
Matsuzawa et al Agric Biol Chem 47(1) pp. 25–28 (1983).
Cowan et al Biochem J. (1987) 247 pp. 121–133.
Bryant et al, "Characterization of hydrogenase from the Hyperthermophilic Archaebacterium, Pyrococcus furiosus", The Journal of Biological Chemistry, vol. 264, No. 264, No. 9, Issue of Mar. 25, pp. 5070–50079.
Aono et al, "A Novel and Remarkably Thermostable Ferrodioxin from the Hyperthermophilic Archaebacterium Pyrococcus furiosus", Journal of Bacteriology, Jun. 1989, pp. 3433–3439, vol. 171, No. 6.
Kelly et al, "Extremely Thermophilic Archaebacteria: Biological and Engineering Considerations", Biotechnology Progress (vol. 4, No. 2, Jun. 1988, reprinted from Chemical Engineering Progress, Aug. 1988, pp. 47–62.
Brown et al, "Cultivation Techniques for Hyperthermophilic Archaebacteria: Continuous Culture of Pyrococcus furiosus at Temperatures near 100 C", Appl'd and Environmental Microbiology, Aug. 1989, vol. 55, No. 8, pp. 2086–2088.
Parameswaran et al, "Engineering Considerations for Growth of Bacteria at Temperatures Around 100C", The Humana Press Inc., Copyright 1988, pp. 53–73.

(List continued on next page.)

*Primary Examiner*—Herbert J. Lilling
*Attorney, Agent, or Firm*—Cushman, Darby & Cushman

[57] ABSTRACT

Cell-free extracts from *Pyrococcus furiosus* were found to possess unusually high levels of proteolytic activity as measured by hydrolysis of azocasein; loss in activity was only 30% after incubation for 24 hours at 98° C. and the half-life of proteolytic activity at that temperature was about 60 hours. Furthermore, cell-free extracts incubated at 98° C. in 1% sodium dodecyl sulfate (SDS) for 24 hours yielded an SDS-resistant protease having a temperature optimum of at least 100° C. The enzyme retained at least 40% of its activity when tested at 98° C. by azocasein hydrolysis in the presence of 4M urea, 2M guanidinium chloride, 10 mM dithiothreitol or 150 mM $\beta$-mercaptoethanol. The protease was found to have a pH optimum of 6.8 at 98° C. and retained more than 45% of its activity at pH 9.3 and 82% of its activity at pH 4.5 in assays performed at those values. The protease was classified as a metalloprotease through inhibitor studies, and peptide hydrolysis showed trypsin-like cleavage with additional activities.

8 Claims, 8 Drawing Sheets

OTHER PUBLICATIONS

Cowan et al, "An extremely thermostable extracellular proteinase from a strain of the archaebacterium Desulfurococcus growing at 88 C", Biochem. J. (1987) 247, 121–133, pp. 121–133.

Matsuzawa et al, "Production of Thermophilic Extracellular Proteases (Aqualysins I and II) by Thermus aquaticus YT-1, an Extreme Thermophile", Agric. Biol. Chem. 47 (1), 25–28, 1983.

Khoo et al, "Interactions of calcium and other metal ions with caldolysin, the thermostable proteinase from Thermus aquaticus strain T351", Biochem. J. (1984) 221, 407–413.

DSM Catalogue of Strains 1989, Pyrococcus Furiosus Stetter and Fiale 2986; Media #377 Pyrococcus/Staphylothermus Medium, pp. I–VIII; p. 97.

Zillig et al, Pyrococcus woesei, sp.nov., an Ultra-Thermophilic Marine Archaebacterium, Representing a Novel Order, Thermococcales, System Appl. Micro Biol. 9, 62–70 (1987).

Matsubara, Methods in Enzymology, vol. XIX, Protolytic enzymes, 1970 Academic Press, N.Y. "Purification and Assay of Thermolysin", 642–650.

Fiala et al, "Pyrococcus furiosus sp.nov. represents a novel genus . . . ", Arch microbiol (1986) 145: 56–61.

Crueger et al, "Biotechnology: A textbook of Industrial Microbiology", Brock, ed., pp. 98–99 (1984).

PROTEOLYTIC ENZYMES FROM HYPERTHERMOPHILIC BACTERIA AND PROCESSES FOR THEIR PRODUCTION

This is a division of application Ser. No. 07/406,327, filed Sep. 12, 1989, now U.S. Pat. No. 5,242,817.

BACKGROUND OF THE INVENTION

The present invention relates to proteolytic enzymes obtainable from hyperthermophilic bacteria and processes for producing them.

Hyperthermophilic bacteria, i.e. bacteria which thrive on temperatures around the boiling point of water, are found in the ocean close to geothermal springs. Since these bacteria live in high temperature environments, their enzymes which are essential to sustaining life, such as digestion and respiration, must be able to function at such extreme temperature conditions. Enzymes in common mesophilic bacteria (i.e., an organism that can grow at intermediate temperatures compared to the upper and lower extremes for all organisms) degenerate rapidly at such high temperatures.

Proteins which can function at high temperatures can be extremely advantageous for use in a number of industries. For example, soda syrup, laundry detergent, and many pharmaceuticals contain, or are manufactured by, enzymes extracted from bacteria. If enzymes from hyperthermophilic bacteria were used in place of the enzymes commonly used today, the processes to make these products could be performed at higher temperatures. Higher temperatures speed up reactions and prevent contamination by fungi and common bacteria. Alternatively, lesser amounts of the enzymes from hyperthermophilic bacteria might be required to sustain enzymatic processes under current temperature conditions, where the thermostability of such enzymes correlates with a longer useful life under those conditions.

A number of microorganisms capable of growth at or above 100° C. (i.e., hyperthermophiles) have been isolated from several terrestrial and marine environments and are of considerable scientific interest. (See Kelly, R. M., and J. W. Deming, 1988, "Extremely Thermophilic Archaebacteria: Biological and Engineering Considerations", Chem. Engr. Prog. 4:47–62; and Wiegel J., and L. G. Ljungdahl, 1986, "The Importance of Thermophilic Bacteria In Biotechnology," CRC Crit. Rev. Microbiol. 3:39–107.) However, it has not previously been possible to take full advantage of the utility potential of these organisms, in large part, because of a lack of understanding of their growth and metabolic characteristics.

Detailed study of specific enzymes from hyperthermophiles is just beginning, and the few known reports on such enzymes that have been published so far all appeared in 1989. For example, it has bean shown (Pihl, T. D. et al., 1989, Proc. Natl. Acad. Sci. 86:138–141) that an extremely thermostable hydrogenase isolated from *Pyrodictium brockii* is immunologically related to the comparable enzyme in the *Bradyrhizobium japonicum*, a mesophile. Adams and coworkers have described several distinctive characteristics of a hydrogenase (Bryant, F. O. & Adams, M. W. W., 1989, J. Biol. Chem. 264:5070–5079) and a ferredoxin (Aono, S., et al., 1989, J. Bacteriol. 171:3433–3439) from the hyperthermophilic bacterium, *Pyrococcus furiosus*.

Proteases are important physiologically in protein digestion and turnover within a cell and industrially for degrading various proteinaceous materials [Kalisz, H. M., 1988, In Advances in Biochemical Engineering/Biotechnology Vol. 36 (Ed. Fiechter, A.), 1–65, Springer-Verlag, Berlin and Heidelberg]. Serine proteases, which includes subtilisin-like proteases and proteinase K, show unusual resistance to denaturation by urea, guanidinium chloride, sodium dodecyl sulfate (SDS), and other detergents [Weber, K., Pringle, J. R. & Osborn, M., 1972, In Methods in Enzymology Vol. 26, Part C (Ed. C. H. W. Hirs & S. N. Timasheff), 3–27 (Academic Press, New York and London]. For example, Deane et al. (1987, J. Gen. Microbiol. 133:2295–2301) reported an SDS-resistant protease from *Vibrio alginolyticus* which is active at 37° C. and alkaline pH, and through inhibitor studies, categorized it as a serine protease (Deane, S. M., et at., 1987, J. Gen. Microbiol. 133:391–398). The approximate molecular weight of this protease was 54,000 daltons based on electrophoresis in SDS, and it was active in the presence of SDS at 37° C. Active fragments (with MW's of 41,000 and 37,000 daltons) of the protein formed when it was dialyzed against distilled water.

Some proteases have been reported that show unusual thermostability. For example, Cowan et al. (1987, Biochem. J. 247:121–133) recently described the discovery of an extracellular protease from a Desulfurococcus species which has a half-life of seventy to ninety minutes at 95° C. but denatures rapidly above 100° C. It is believed that this represents the most extreme thermostability yet reported for a proteolytic activity. Other similarly thermostable proteases, primarily from Thermus species, have also been described (Cowan, D. A. & Daniel, R. M., 1982, Biochim. Biophys. Acta 705:293–305; Khoo, T. C., et al., 1984, Biochem. J. 221:407–413; Taguchi, H., et al., 1983, J. Biochem. 93:7–13; Matsuzawa, H., et al., 1983, O. Agric. Biol. Chem. 47:25–28). Proteases from hyperthermophilic bacteria, however, do not appear to be known in the art.

Accordingly, a major object of the present invention is to provide methods for producing proteolytic enzyme preparations from hyperthermophilic bacteria such as *P. furiosus*.

It is also an object of the present invention to provide purified proteolytic enzyme preparations exhibiting thermostable activities that are resistant to detergents and thus are useful for various industrial applications.

SUMMARY OF THE INVENTION

The present invention is based, at least in part, on the finding that hyperthermophilic bacteria, for example, *Pyrococcus furiosus*, can be continuously cultivated at temperatures approaching 100° C. (e.g., 97°–99° C.), to provide useful enzymes at a highly desirable rate. In particular, the present inventors have found that *P. furiosus* produces several intracellular and extracellular proteases which retain their activity for several hours at about 100° C.

Accordingly, in one aspect the present invention relates to a proteolytic enzyme preparation that is obtainable from the hyperthermophilic bacterium *Pyrococcus furiosus* by a process comprising the steps of cultivating cells of the bacterium in nutrient medium, collecting the cells from the medium, disrupting the cells, and removing the resulting insoluble cell debris.

The resulting soluble cell-free extract constitutes a proteolytic enzyme preparation that includes five active proteolytic enzyme species which by electrophoretic mobility have the following approximate molecular mass values in kilodaltons (kDa): 140; 125; 116; 102; and 66.

In another aspect, this invention also relates to a proteolytic enzyme preparation obtainable from the hyperthermophilic bacterium *Pyrococcus furiosus* by a process comprising the steps of cultivating cells of the bacterium in nutrient medium, removing the cells from that medium, and isolating the proteolytic enzyme from the remaining liquid. Although not fully characterized, such medium from *Pyrococcus furiosus* cultures has been found to contain several distinct species of proteolytic enzymes, some of which, at least, are also be obtainable from disrupted cells.

The cell-free preparation of proteolytic enzymes of this invention has a remarkable resistance to inactivation by heat that is characterized by a half-life of proteolytic activity at 98° C. of about 60 hours. For comparison, as indicated in the Background, it is believed that the most extreme thermostability previously reported for a proteolytic activity was characterized by a half-life of 70 to 90 minutes at 95° C.

Accordingly, the present invention also relates to a thermostable cell-free proteolytic enzyme preparation having a half-life of proteolytic activity at 98° C. of about 60 hours. Advantageously, this preparation is derived from a hyperthermophilic bacterium or medium in which the hyperthermophilic bacterium has been cultivated.

The cell-free proteolytic enzyme preparation of the present invention further has resistance to inactivation by the strong ionic detergent, sodium dodecyl sulphate (SDS), at a concentration of 1% by weight, that is characterized by a half-life of proteolytic activity at 98° C. of about 12 hours.

In another aspect, the present invention relates to a process for obtaining a purified proteolytic enzyme preparation from a hyperthermophilic bacterium, which comprises the steps of cultivating cells of the bacterium in nutrient medium, disrupting the cells, and incubating the resulting cell extract at about 100° C. for a time period in the range of about 1 hour to about 105 hours.

In this process according to the present invention, the thermostable proteolytic enzymes of the bacterium are purified by virtue of their own proteolytic activity which hydrolyses essentially all other cellular proteins. This digestion of the disrupted cells may be facilitated advantageously by addition of a detergent, such as SDS, to which the proteases of this invention are also highly resistant, as noted above. The amount of SDS used can be varied from about 0.1% (weight/volume) to at least 2%, with decreasing incubation time at about 100° C. being required for digestion of cellular proteins.

In any event, the maximum time of incubation for preparation of purified enzymes according to the present invention is determined by the amount of enzymatic activity that is desired to remain after this purification process; while the minimum acceptable level is determined by the amount of residual cellular protein that is acceptable. The Examples below provide specific conditions and characteristics of the preparations made under those conditions.

According to a major embodiment of this aspect of this invention, this proteolytic enzyme purification process is applied to the hyperthermophilic bacterium *Pyrococcus furiosus*. The present invention, however, also contemplates the use of this novel proteolytic enzyme purification process for isolation of thermostable proteolytic enzymes from other hyperthermophilic bacteria. In fact, one important use of this method, aside from simple and inexpensive large scale production of purified proteases, is in the screening of cultures of previously untested hyperthermophilic bacteria for the presence of thermostable proteolytic enzymes that are distinct from those of *Pyrococcus furiosus* and, therefore, may have different utilities.

This process of obtaining a purified proteolytic enzyme from a hyperthermophilic bacterium, such as *Pyrococcus furiosus*, for instance, is advantageously coupled with a method for continuous steady-state culture of such organisms which has been developed by the present inventors. The yields per unit of culture medium and the reductions in labor and downtime for equipment cleaning of this approach compare quite favorably to the more usual batch approaches for cultivation of bacteria which grow only at lower temperatures.

An embodiment of this overall enzyme production method which incorporates this simple continuous culture method is described below for cultivating hyperthermophilic bacteria at a temperature of about 98° C. at ambient pressure under conditions of continuous steady-state culture. In the case of *Pyrococcus furiosus*, the atmosphere is maintained in an anaerobic state and the nutrient medium comprises sea water (either artificial or natural) containing complex carbon sources, such as those known in the art for other heterotrophic bacteria. Optionally, for better growth, elemental sulphur is added at about 10 grams per liter.

In yet another aspect, the present invention relates to a purified proteolytic enzyme preparation obtainable from a hyperthermophilic bacterium by the process described above. A preferred embodiment of this aspect of this invention is exemplified by a purified proteolytic enzyme preparation obtainable from the hyperthermophilic bacterium *Pyrococcus furiosus* by a process comprising the steps of cultivating cells of the bacterium in nutrient medium, disrupting the cells, removing the resulting insoluble cell debris by centrifugation, adding 1% by weight of sodium dodecyl sulphate to the disrupted cells, and incubating the resulting cell extract at about 100° C. for a time period in the range of about 12 to 24 hours. Experimental data presented below indicate that the vast majority of the cellular proteins are digested by this procedure such that they are no longer detectable, for example, by electrophoresis in polyacrylamide gels.

The purified proteolytic enzyme preparation prepared according to this method of the invention, which is also called "Pyrolysin" by the inventors, comprises varying amounts of any of two active proteolytic enzyme species distinguished by approximate molecular mass values of about 70 kDa and about 55 kDa.

The purified proteolytic enzyme preparation described above has a pH optimum at 98° C. for proteolytic activity of about pH 6.8, and shows approximately half-maximal activity over the range of about pH 4.0 to pH 9.0 during 30 minute assays. Further, this preparation retains about 2% of original activity after incubation at about pH 9.3 for 3 hours.

Further, this purified proteolytic enzyme preparation of the present invention has resistance to inactivation by either 1 molar urea or 1 molar guanidinium chloride that is characterized by no loss of proteolytic activity at 98° C. for at least 30 minutes.

The present invention may be understood more readily by reference to the following detailed description of specific embodiments and the figures and examples included therein.

DESCRIPTION OF SPECIFIC EMBODIMENTS

The present invention relates to a proteolytic enzyme preparation obtainable from the hyperthermophilic bacterium *Pyrococcus furiosus* by a process comprising the steps of cultivating cells of the bacterium in nutrient medium, collecting the cells from the medium, disrupting the cells, and removing the resulting insoluble cell debris.

In a preferred embodiment of this aspect of this invention, the *Pyrococcus furiosus* is the strain of deposit DSM 3638 of the Deutsche Sammlung yon Mikroorganismen, Federal Republic of Germany. This deposit is accessible to the public without restriction. Accordingly, access to the deposit by the Commissioner during pendency of this application, "reasonable" permanent availability of the culture, and access to the culture by the public upon issuance of the patent are all assured by means of this deposit.

The present invention is based, at least in part, on the finding that hyperthermophilic bacteria, for example, *Pyrococcus furiosus*, can be continuously cultivated at temperatures approaching 100° C. (e.g., 97°–99° C.), to provide useful enzymes at a highly desirable rate. The general growth characteristics of *P. furiosus*, a heterotrophic anaerobe isolated by Stetter and Fiala (Fiala, G. & Stetter, K. O., 1986, Arch. Microbiol. 145:56–61) from shallow thermal waters near Vulcano Island, Italy, have been described previously (Brown, S. H. & Kelly, R. M., 1989, Appl. Environ. Microbiol. 55:2086–2088). Specific details of cultivation media and methods developed for production of enzymes from *P. furiosus* cells, either in batch cultures or under continuous, steady-state conditions, are described in Example 1, below.

According to this aspect of the present invention, a cell-free preparation of proteolytic enzymes is exemplified by a soluble *P. furiosus* cell extract that is prepared by collecting the cells from the culture medium by centrifugation, disrupting the cells by sonication, and removing the resulting insoluble cell debris by high speed centrifugation, as described in further detail in Example 2.

Proteolytic activity in the cell-free extracts from *P. furiosus* increased from 37° C. to 105° C.; the activity at 37° C. was 5.9% of the activity at 100° C. Although activity appeared to be still increasing at 105° C., the temperature optimum for the proteolytic activity of this extract cannot be determined reliably from the standard assays used for known proteases (e.g., using azocasein substrate) due to rapid abiotic breakdown of the usual substrates at temperatures in excess of 100° C. Accordingly, the optimum is not yet known for this extract or its individual components.

Figure 1:
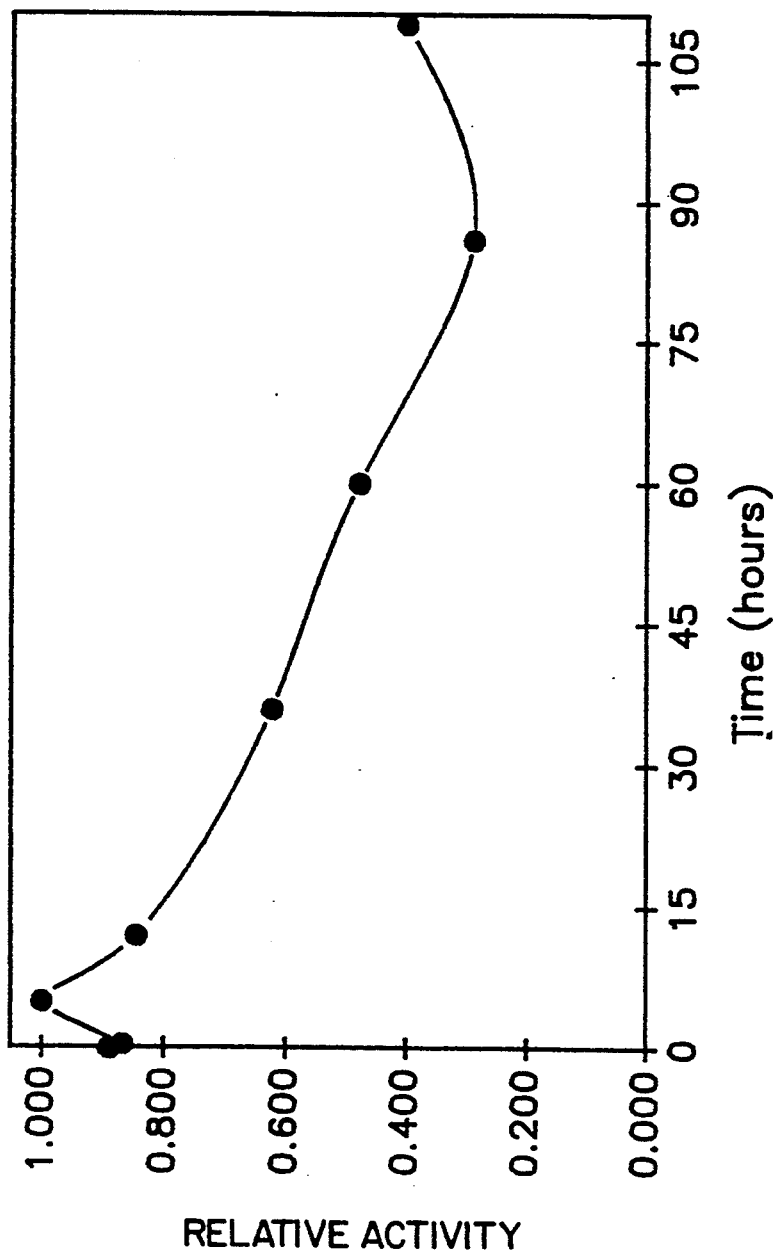
FIG. 1. Thermostability of proteolytic enzyme activity in cell-free extract of *Pyrococcus furiosus*. Samples of cell-free extract preparation were incubated at 98° C. for the specified times prior to assay at 98° C. by the standard assay using azocasein substrate.

The half-life of total proteolytic activity in the *P. furiosus* cell-free extract at 98° C. was over sixty hours under the standard assay conditions, as calculated from the inactivation data in FIG. 1.

SDS-PAGE gels containing 0.1% gelatin (Hare, P., et al., 1983, J. Gen. Microbiol. 129:1141–1147) were used to identify activity associated with individual species of proteases. In this method, if proteases are active during the electrophoretic separation, they will leave a trail of digested gelatin which, upon staining of the gels for protein, will appear unstained against a darkly stained background. In the present case, staining of the gelatin-containing gel revealed a broad zone of proteolytic activity from the top of the gel to a point corresponding to approximately 140 kDa, followed by several apparent bands that could not be clearly distinguished against the background of clearing.

Proteolytic enzyme activities were also detected in the culture medium of *P. furiosus* cells after their removal by centrifugation and concentration of the cell-free medium by cross-current filtration. These preparations produce patterns in gelatin-containing SDS-PAGE gels that were similar to those patterns produced by soluble extracts of cells, indicating that the cell-free culture medium is also a useful source of proteolytic enzymes. Additional testing shows that the cell-free culture medium contains at least the same SDS-resistant proteolytic enzyme activities that are purified from cell extracts by heating at 98° C. in SDS (as described below), as well as additional components that have not been further characterized.

A second approach to identifying individual active species was used, in which proteolytic enzymes are first separated by SDS-PAGE in the absence of substrate and then transferred to a gel containing gelatin that was overlaid to determine positions of proteolytic activity. In this method, sharp bands of proteolytic activity were evidenced by cleared (white) bands resulting from the gelatin cleavage in the otherwise darkly stained overlay gel (see FIG. 2). In samples of the cell-free extract, five distinct bands with proteolytic activity are found with the following approximate molecular mass values in kilodaltons (kDa): 140; 125; 116; 102; and 66.

It will be appreciated by one skilled in the art of protein biochemistry that molecular mass determinations by comparison to standards in SDS-PAGE analyses are subject to certain well known sources of imprecision. In the present case, an additional practical difficulty arises if molecular weight markers in a stained gel are compared to activity bands in a gelatin overlay gel. Since the two gels shrink slightly differently during the staining and destaining procedures, the positions of molecular mass markers in the gels that are directly stained with dyes to detect proteins are not directly comparable to positions of bands with proteolytic activities in the gelatin substrate overlay gels. Accordingly, the approximate molecular mass values cited herein are determined by staining a single gel that contains both molecular mass markers and proteolytic enzyme preparations in adjacent lanes, which had been overlaid with a gelatin substrate gel. After the transfer step is completed and the overlay gel is removed, both the original gel and the overlay gel are stained. The original gel then shows a background of stained gelatin, albeit lighter than the overlay gel, against which faint cleared zones corresponding to the active proteolytic enzyme species, as well as the darkly stained bands of the molecular mass markers, are both readily discernible. For a more visible photographic presentation of the active proteolytic enzyme species, however, the overlay gel is required and has been used in FIG. 2 of this application.

Proteolytic enzyme activities may be characterized in part by sensitivity to inhibitors which a directed to different moieties in the active sites of various proteases.

The sharp bands in the substrate overlay gels correspond to the clearing zones noted in the SDS-PAGE gels that contained gelatin. This implied that, indeed, certain proteases were active during the SDS-PAGE separation. It was concluded, therefore, that at least one of the proteases in the cell-free extract was SDS-resistant, behaving similarly during electrophoresis to the SDS-resistant protease from V. alginolyticus (Deane, S. M., et al., 1987, J. Gen. Microbiol. 133:2295–2301).

Accordingly, to investigate the nature of the SDS-resistant proteolytic activity in P. furiosus cell-free extracts, samples of the extract were incubated with 1% SDS at 98° C. for various periods of time, as described in Example 3. Essentially complete proteolytic activity in the extract was retained after incubation for ten minutes. After 12 hours in 1% SDS at 98° C., 47.5% of the initial activity remained, and after 24 hours, 19% of the initial activity remained, as measured by azocasein cleavage.

Figure 2:
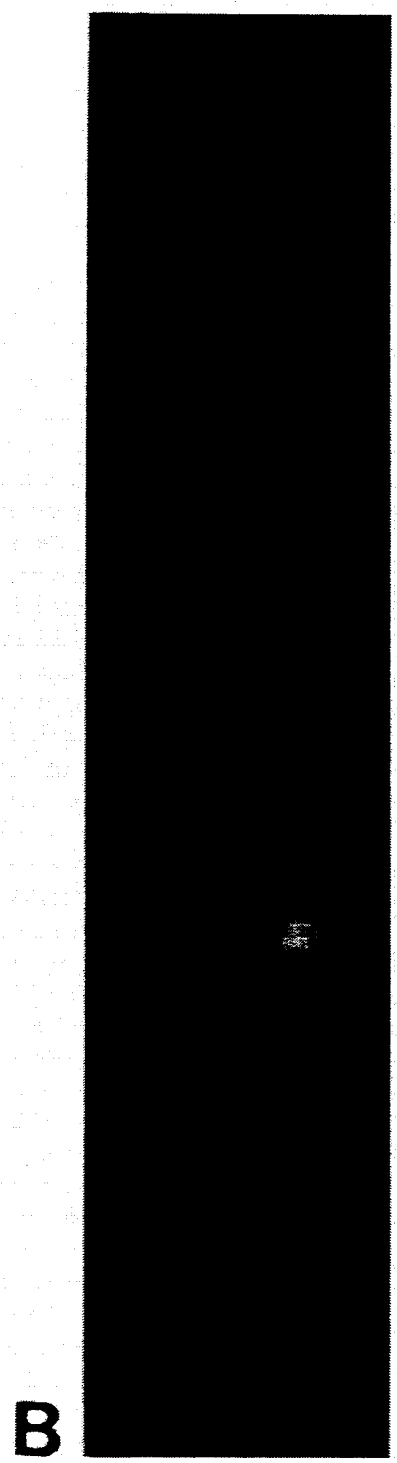
FIG. 2. Identification of active proteolytic enzyme species in the cell-free extract of *Pyrococcus furiosus* by electrophoresis in polyacrylamide gels (PAGE) containing SDS and overlaying with a another gel containing gelatin substrate. The gel shown is a gelatin-containing overlay gel in which the gelatin is darkly stained by dye that stains all proteins, except for light zones representing clearing of the gelatin by active proteolytic enzyme species. The samples in the gel are: soluble extract (XTR) and SDS-resistant purified preparation (SDS). Estimated mass values of the active proteolytic species in the cell-free extract are, in kilodaltons (kDa): 140; 125; 116; 102; and 66 (see Description of Specific Embodiments for details on the method used to obtain these values).

Proteolytic enzyme activity in the presence of SDS caused cleavage of the vast majority of the proteins in the extract, leaving after 24 hours at 98° C., essentially two predominant species of proteolytic enzyme with activity, as demonstrated by overlaying a polyacrylamide gel with a gelatin-containing gel (see FIG. 2, SDS samples). The approximate molecular masses on SDS-PAGE, of the SDS-resistant proteolytic enzyme species purified from cell-free extracts in the above manner are about 102 kDa and 66 kDa.

Figure 3:
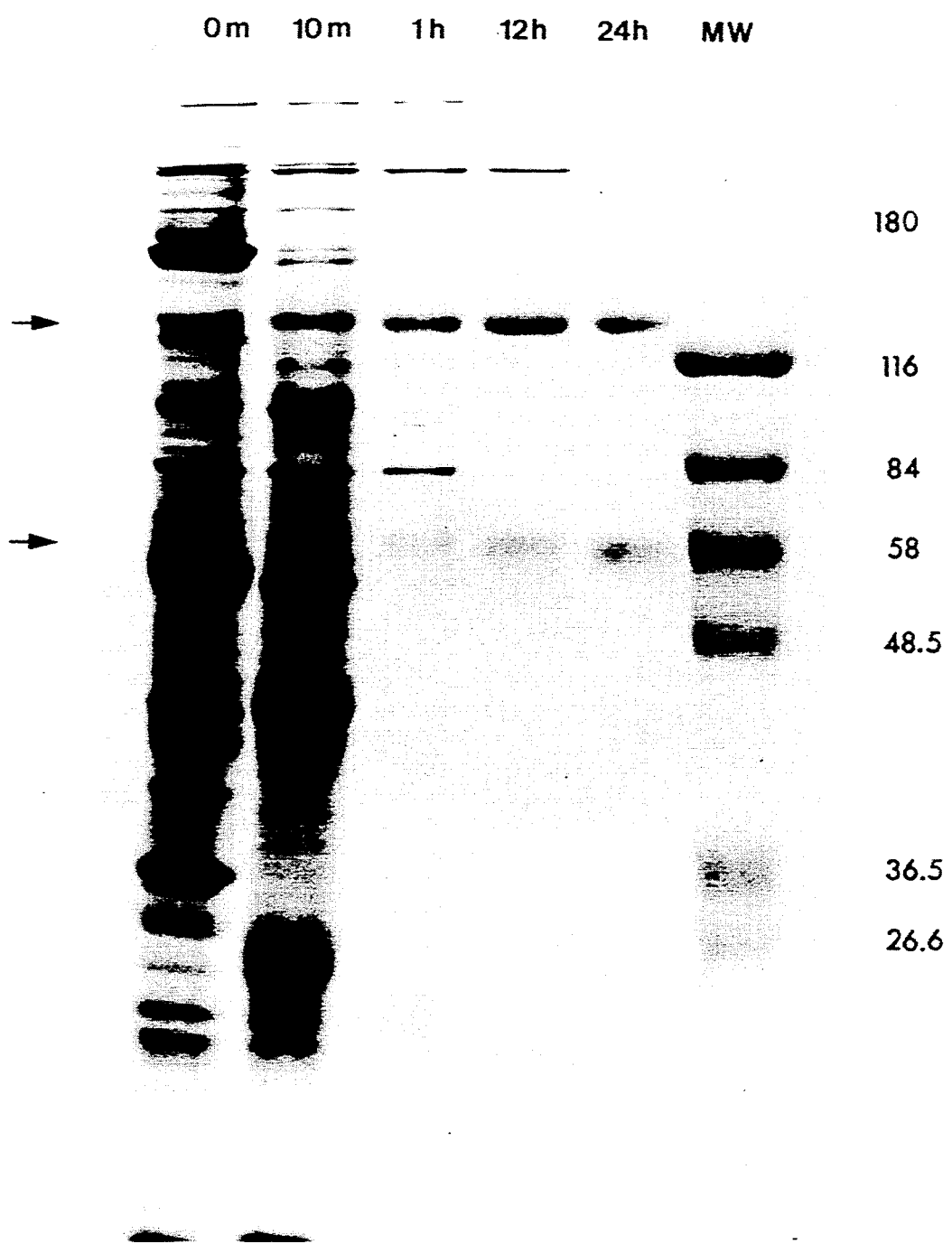
FIG. 3. Time course of cellular protein digestion during purification of SDS-resistant proteolytic enzyme preparation from *Pyrococcus furiosus* cell extract by incubation at 98° C. in 1% SDS. Samples taken at 0 min, 10 min, and 1 h, 12 h and 24 h(ours) were cooled to 4° C., separated by SDS-PAGE Proteins were then stained with Coomassie blue-amido black.

The protein content of the extract containing 1% SDS drops dramatically at 98° C. within the first hour, with less than 10% of the original protein species distinguished by SDS-PAGE remaining (see FIG. 3). By 24 hours under these conditions, two predominant protein bands are readily detectable by usual protein staining methods. These two stained bands have apparent molecular masses of about 140 kDa and 66 kDa. A faint band of approximately 240 kDa is also detectable in most preparations.

It should be noted that at least one of the proteolytic activity bands from the purified SDS-resistant preparation shows not corresponding band in gels that are simply stained to detect protein bands. This is consistent with the fact that the staining method for detecting protein mass is known to be considerably less sensitive than many enzymatic activity assays. In addition, the 204 kDa and 140 kDa species that are detectable in the SDS-resistant purified preparation by protein staining do not appear to be active proteolytic enzyme species under the experimental conditions used in these studies. Finally, although the protein staining band and the proteolytic activity band with the lowest mass both appear to have a mass of about 66 kDa, it remains to be determined what portion of the stained protein actually represents the 66 kDa active proteolytic enzyme species.

Similar kinetic experiments on the proteolytic digestion of cellular proteins in the cell-free extract of P. furiosus were preformed in the absence of SDS. The results indicate that an incubation of about 105 hours produces results essentially equivalent to 24 hours in the presence of 1% SDS, in terms of both the total activity remaining and the distribution of activity in the two remaining active species detectable by SDS-PAGE.

Figure 4:
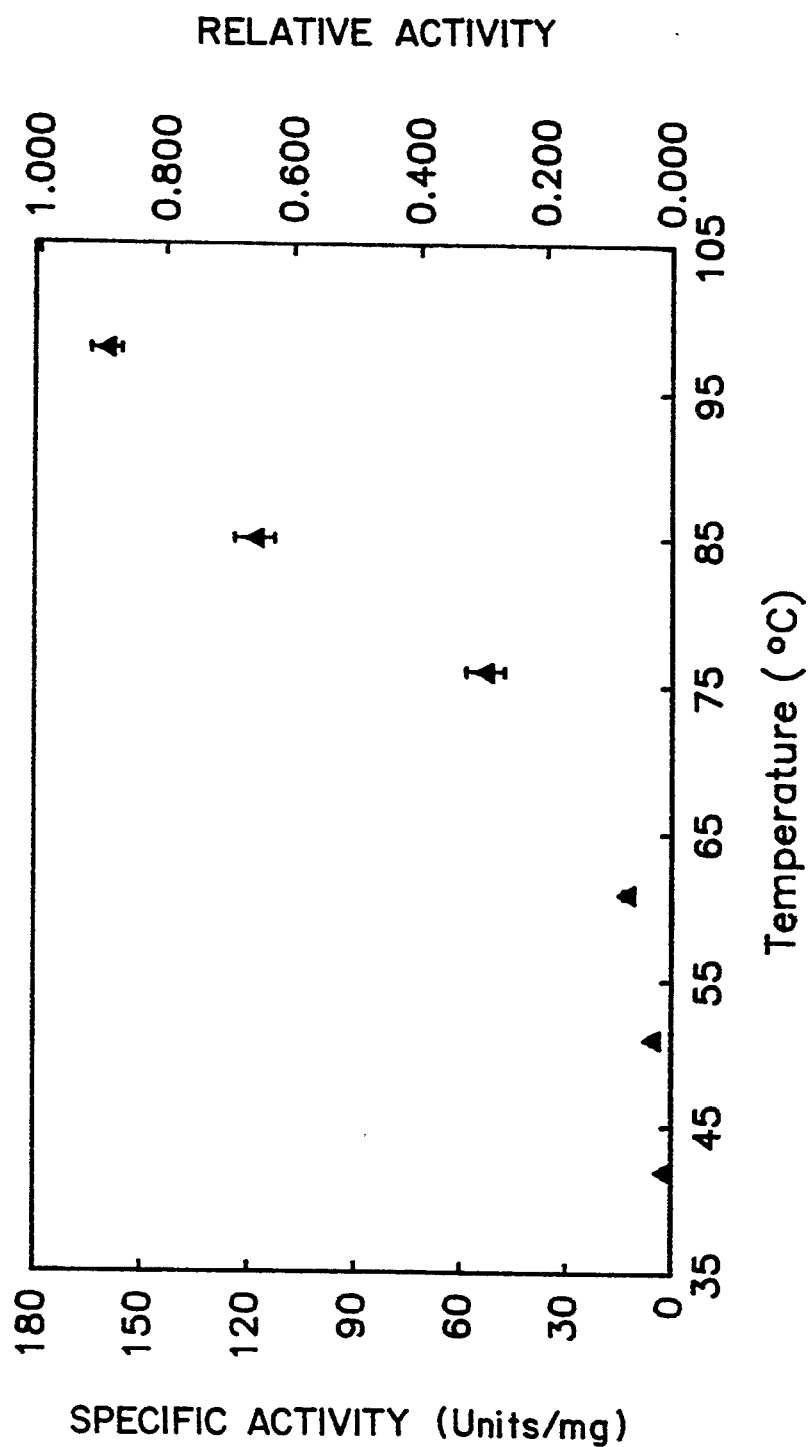
FIG. 4. Effect of temperature on activity of purified SDS-resistant proteolytic enzyme preparation from *Pyrococcus furiosus*. The standard (azocasein) reaction mixtures were incubated for 30 min. at each indicated temperature. Six points (duplicates of three protein concentrations) were measured at each temperature, the deviation being represented by the error bars on the graph.

FIG. 4 shows the effect of temperature on the proteolytic activity of the purified SDS-resistant protease prepared as described in Example 3. From 40° C. to 90° C. the average $Q_{10}$ value (an indicator of rate of increase in the enzymatic activity as a function of temperature) for azocasein hydrolysis was 2.50; this value fell to 1.05 between 90° C. and 100° C. Because azocasein is increasingly less stable at and above 100° C., measurement of proteolytic activity is less certain although, qualitatively, activity is apparent at least up to 105° C.

The protease shows significant resistance to other denaturing agents, in addition to SDS. Several denaturing agents were added to azocasein, both in the presence and absence of the protease, to control of possible degradation of the substrate in the presence of the agents. The resulting percentages of original activity observed in each case under the standard assay conditions are as follows: No denaturant: 100%; 2M urea: 124%; 4M urea: 138%; 1M guanidinium chloride: 256%; 2M guanidinium chloride: 299%; 10 mM dithiothreitol (DTT): 39.5%; 10 mM DTT+4M urea: 63%; 150 mM β-mecaptoethanol: 57%. Thus, high concentrations of urea and guanidinium chloride led to significant abiotic hydrolysis of azocasein such that results were difficult to interpret. The increases in relative activity above 100% are likely the result of the denaturing agents acting to make the azocasein substrate more susceptible to enzymatic hydrolysis.

It is possible that disulfide bonding is important in maintaining the proteolytic activity of at least one active species in the purified SDS-resistant preparation, because dithiothreitol and β-mercaptoethanol adversely affected activity. Urea and guanidinium chloride, known to disrupt hydrogen bonding in proteins, apparently have little effect.

Figure 5:
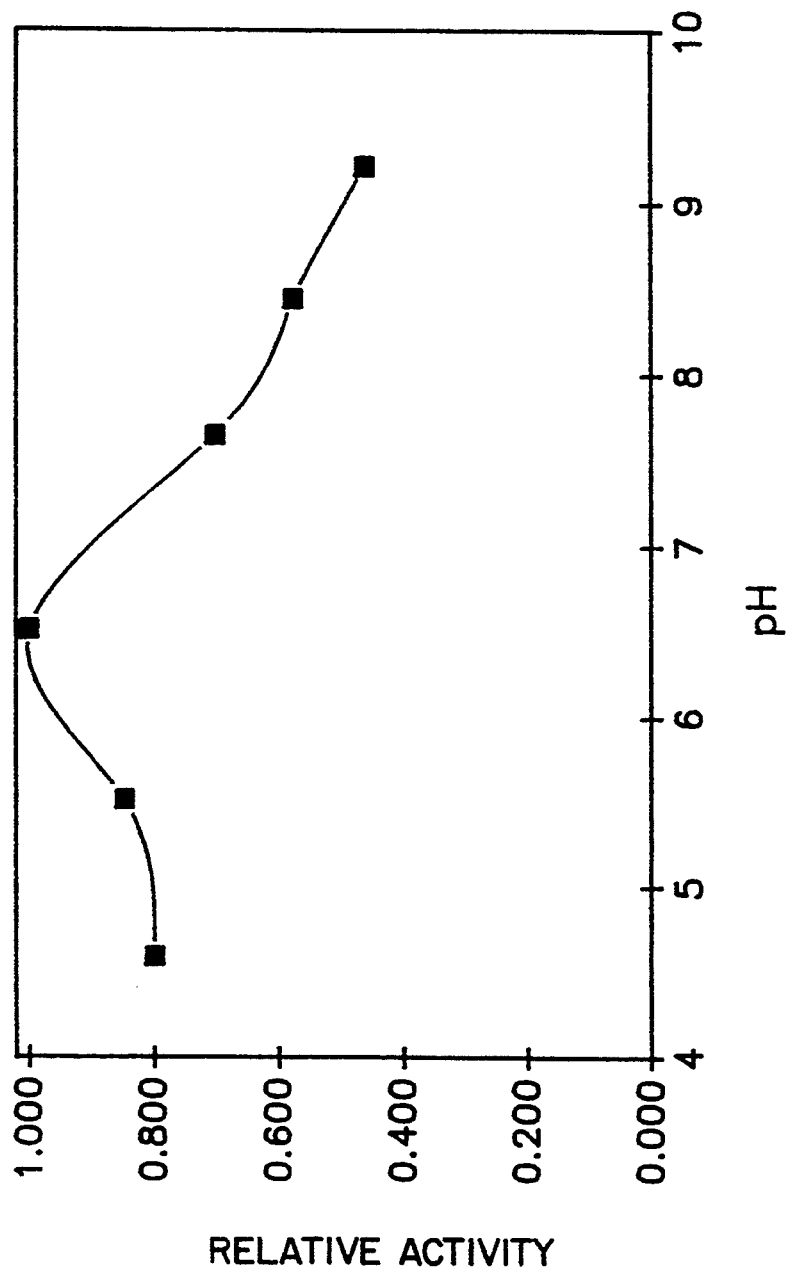
FIG. 5. Effect of pH on activity at 98° C. of purified SDS-resistant proteolytic enzyme preparation from *Pyrococcus furiosus*. Samples of purified enzyme preparation were assayed in 50 mM sodium phosphate buffer at the pH values indicated.
Figure 6:
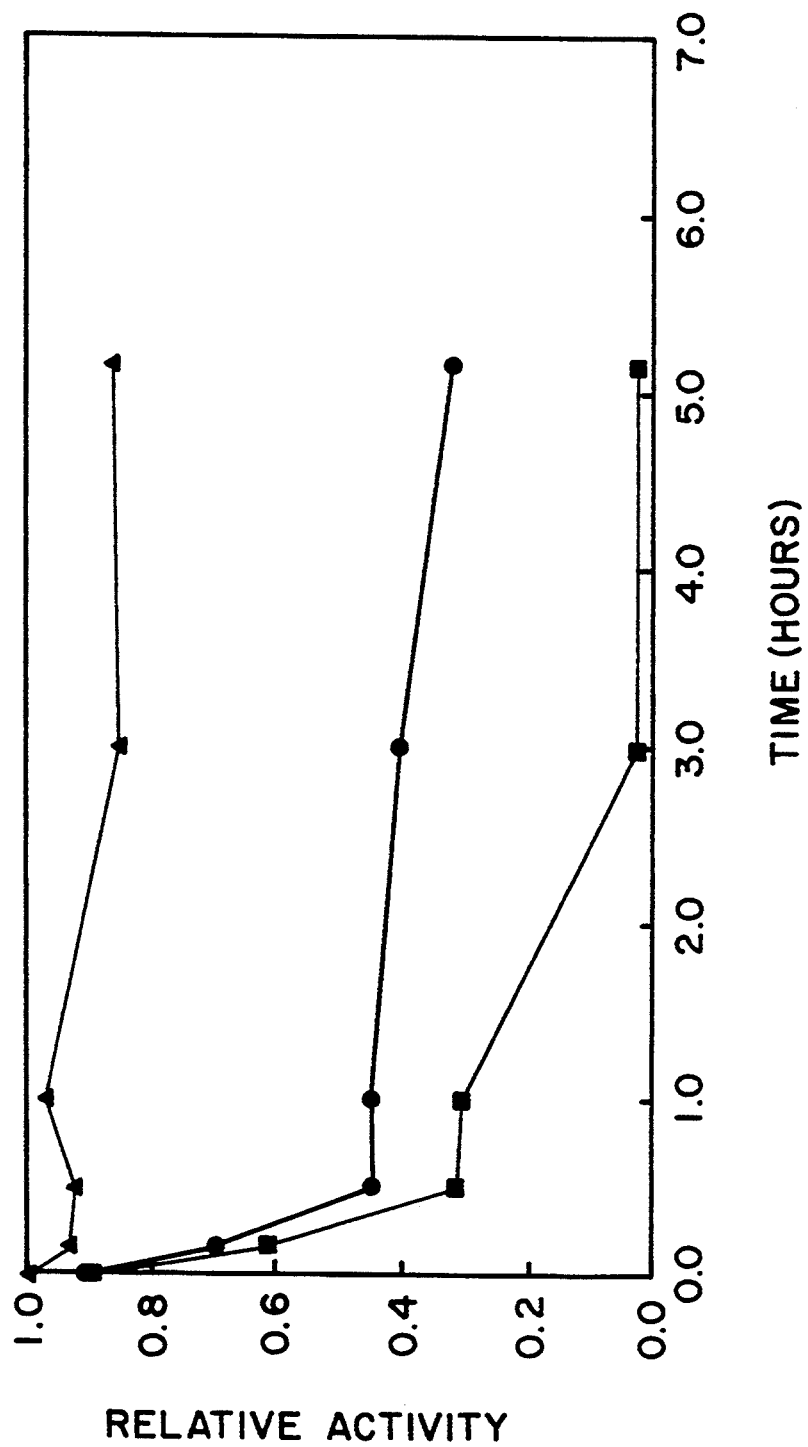
FIG. 6. Effect of pH on stability of activity at 98° C. of purified SDS-resistant proteolytic enzyme preparation from *Pyrococcus furiosus*. Samples of purified enzyme preparation were incubated in 50 mM sodium phosphate buffer at the pH values indicated at 98° C. for the specified times prior to standard assay.
Figure 7:
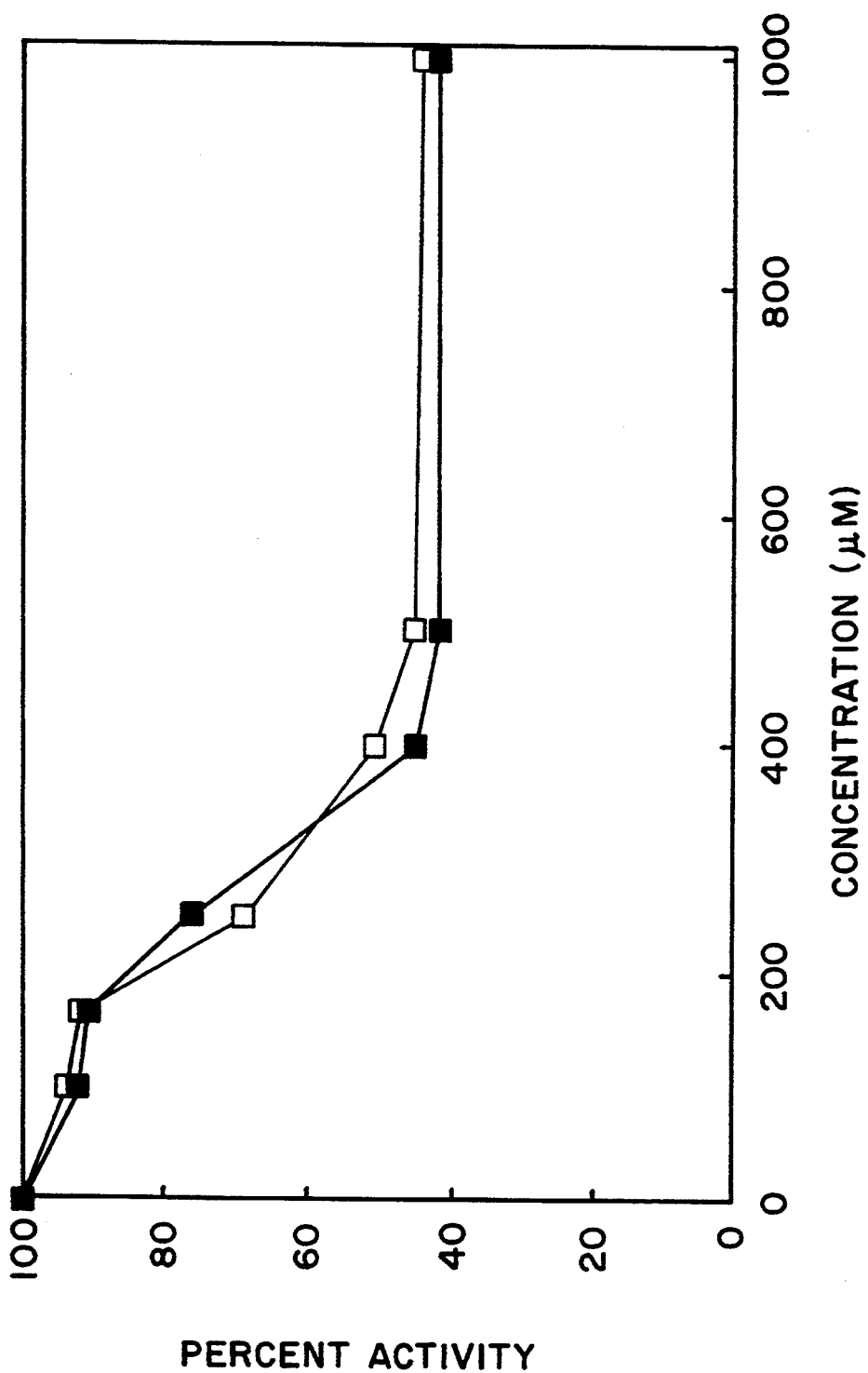
FIG. 7. Effect of chelating inhibitors EDTA and EGTA on activity at 98° C. of purified SDS-resistant proteolytic enzyme preparation from *Pyrococcus furiosus*. Samples of purified enzyme preparation were assayed in the standard azocasein with the inhibitor concentrations indicated.

The purified SDS-resistant preparation also showed activity over the tested pH range, from 4.5 to 9.3. The optimum pH of the enzyme at 98° C. was found to be 6.8 although the activity at pH 4.5 and pH 9.3 was at least 45% of the optimal activity (see FIG. 5). Further, this preparation retains about 2% of original activity after incubation at about pH 9.3 for 3 hours prior to assay. When the pH was dropped to 2 for ten minutes, and then brought back to 7, 25% of the initial activity was lost. If the purified proteolytic enzyme preparation was left at pH 2 for four hours at room temperature, all detectable activity was lost. The stability of activity measured at 98° C. of the purified preparation exposed to pH levels of 4.5, 7.5, and 9.3, is shown in FIG. 6. Despite the drastic drop n activity after one hour at 98° C in pH 9.3, this purified SDS-resistant proteolytic enzyme preparation shows the highest stability to this pH at a temperature of 98° C., even though this is far from its pH optimum.

The results of inhibitor studies on the purified SDS-resistant enzyme preparation are summarized in Table 1.

TABLE 1

Inhibitor studies on purified SDS-resistant proteolytic enzyme preparation.

| Inhibitor | Concentration | % inhibition |
|---|---|---|
| phenyl methyl-sulfonyl fluoride | 10 mM | 0 |
| p-chloromercuri-benzoate | 10 mM | 40* |
| iodoacetic acid | 10 mM | 0 |
| EDTA | 10 mM | 49 |
|  | 500 μM | 51 |
|  | 100 μM | 7.8 |
| EGTA | 10 mM | 49 |
|  | 500 μM | 51 |
|  | 100 μM | 7.8 |

*The solvent for p-chloromercurobenzoate (PCMB), 0.1 N NaOH, inhibited enzyme activity by 50%, and the addition of the PCMB decreased activity by an additional 40%.

Although at least some of the activity in the purified preparation can be classified as that of a metalloprotease for its sensitivity to metal chelators, such as EDTA and [Ethylenebis(oxyethylenenitrilo)]tetraacetic acid (EGTA), it is unclear why there is not complete inhibition at any concentration of the chelators.

Dialysis against EDTA and preincubation for fifteen minutes at room temperature or at 98° C. with all of the tested inhibitors did not increase the inhibition. For EDTA and EGTA, the point of compete saturation (about 50% inhibition) was reached at 400 μM and no inhibition occurred at concentrations below 150 μM.

In hydrolysis experiments on benzoyl DL-arginine p-nitroanilide and benzoyl-L-arginine ethyl ester, there was no product formation at 60° C., 75° C., or 98° C., although trypsin was effective for both synthetic substrates at 60° C.

Figure 8:
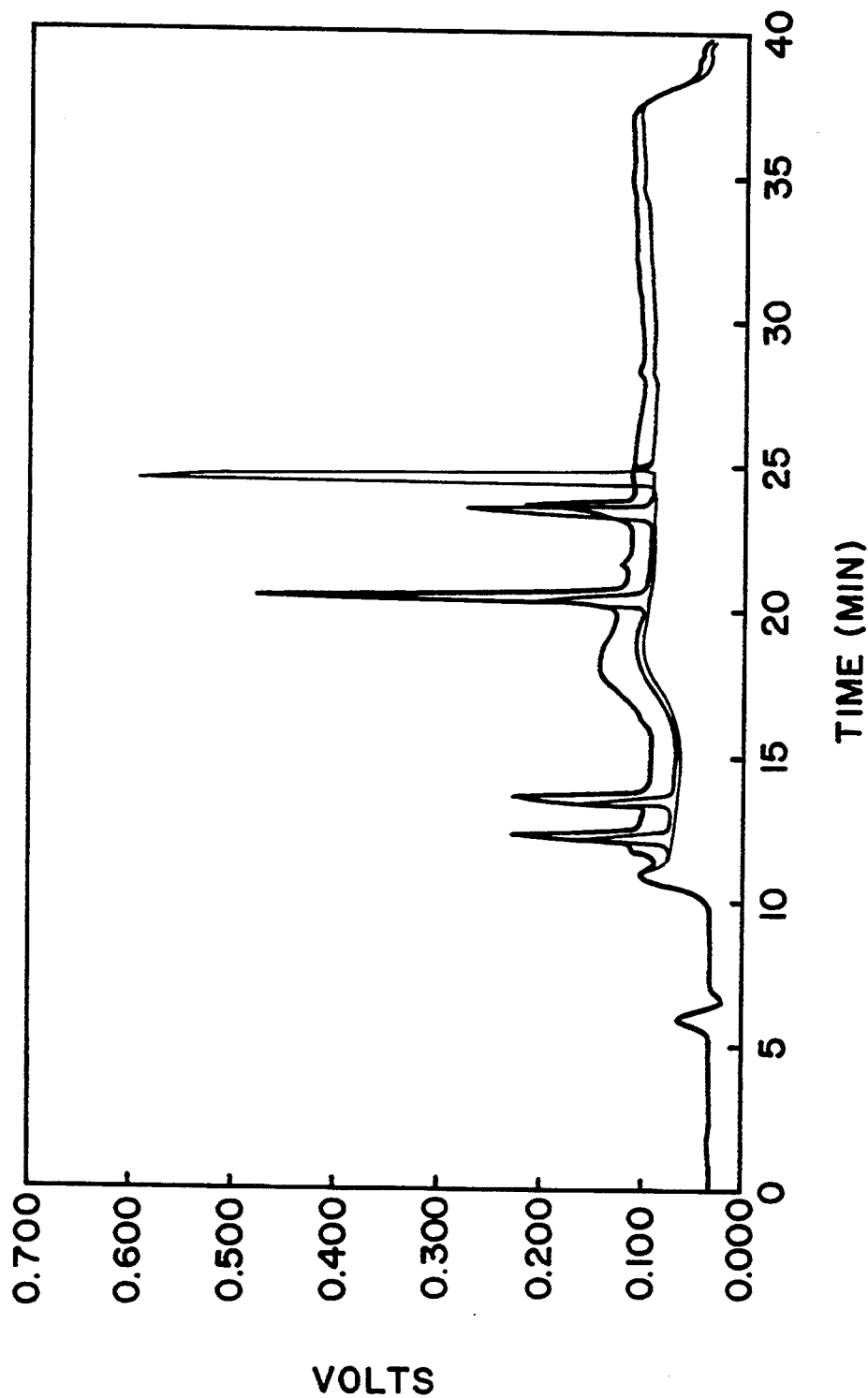
FIG. 8. Comparison of hydrolysis products of angiotensin I polypeptide by trypsin and purified SDS-resistant proteolytic enzyme preparation ("Pyrolysin") showing similarity of cleavage except for one additional cleavage by the novel enzyme preparation.

For two peptides, serum thymic factor and angiotensin I, cleavage products were formed, as visualized by reverse phase separation (described below in Example 3). A chromatogram of the cleavage products of angiotensin I after exposure to the purified P. furiosus protease and to trypsin is shown in FIG. 8. After one hour at 98° C., there is no remaining uncleaved peptide in the case of P. furiosus proteolytic enzyme hydrolysis, although after two hours with trypsin at 40° C. there is still a portion of uncleaved angiotensin I. The similarity of the end product chromatograms of trypsin and the purified P. furiosus proteolytic enzyme preparation indicates that the latter contains at least on species with a trypsin-like specificity of cleavage. FIG. 8 also shows, however, that one angiotensin I fragment that is not cleaved by trypsin is cleaved by the purified P. furiosus preparation. Amino acid analysis shows that this cleavage is at a tyrosine residue. Thus the purified SDS-resistant preparation has activity with at least one additional cleavage specificity that is not exhibited by trypsin.

The purified SDS-resistant preparation also shows remarkable retention of activity in solvents that are used for fractionation of proteinaceous materials or in peptide chemistry, as summarized in Table 2:

TABLE 2

Effects of solvents on purified SDS-resistant proteolytic enzyme preparation.

| Solvent | Concentration | % Activity |
|---|---|---|
| None | — | 100 |
| Acetonitrile | 20% (v/v) | 77 |
|  | 50% | 71 |
|  | 70% | 39 |
| Dimethylformamide | 10% (v/v) | 80 |
|  | 50% | 13 |
|  | 100% | 25 |
| Polyethylene glycol* | 5% (w/v) | 92 |
|  | 10% | 86 |

*PEG-8000 in aqueous solution (standard assay buffer.

EXAMPLE 1

Cultivation of Pyrococcus furiosus for Enzyme Production

A system has been developed which allows continuous cultivation of hyperthermophilic archaebacteria at temperatures approaching 100° C. Using this system, continuous cultivation of the hyperthermophile, Pyrococcus furiosus, was carried out and the resulting dilution rate and gas production profiles are discussed.

The discovery of bacteria which are hyperthermophilic, i.e., have optimal growth temperatures at or above 100° C., has generated considerable scientific interest. However, the biotechnological potential of these organisms has yet to be realized, in large part because of a lack of understanding of their growth and metabolic characteristics. A key factor in the study of these bacteria will be the development of cultivation strategies which will allow exploration of metabolic behaviors and optimization of growth parameters, and at the same time provide sufficient amounts of biomass for further studies. Continuous culture is one mode of operation which meets the above requirements, and in fact is has been used previously in research involving more moderate thermophiles. In this example are results concerning the design and operation of a system which allows continuous cultivation of hyperthermophilic bacteria at temperatures approaching 100° C. These results have been published (Brown, S. H. & Kelly, R. M., 1989, Appl. Environ. Microbiol. 55:2086–2088, the entirety of which is hereby in incorporated herein by reference).

*Pyrococcus furiosus* is a hyperthermophilic archaebacterium which grows optimally at 98°–100° C. This organism was first isolated from shallow geothermal marine sediments by Fiala and Stetter (supra). It is an obligatedly anaerobic heterotroph, and grows in both the presence or absence of elemental sulfur. When sulfur is present, $H_2S$ and $CO_2$ are produced as a consequence of growth, along with trace amounts of $H_2$. In the absence of sulfur, only $CO_2$ are produced, and the $H_2$ eventually becomes inhibitory to cell growth. The relationship between the production of these gases, particularly $H_2S$, and the metabolism of *P. furiosus* has not yet been determined. *P. furiosus* can reach cell densities of over $10^8$ cells/ml, which is relatively high for this class of organisms, making it an attractive candidate for production of enzymes for industrial applications according to the present invention.

*Pyrococcus furiosus* (DSM 3638) was grown in artificial sea water supplemented with 0.1% yeast extract and 0.5% tryptone (Difco Laboratories, Detroit, Mich.). The artificial sea water was modified from Kester et al. (Kester, D. R., et al., 1967, Limnol. Oceanogr. 12: 176–178) and was formulated as follows: Solution A, 47.8 g/l NaCl, 8.0 g/l $Na_2SO_4$, 1.4 g/l KCl, 0.4 g/l $NaHCO_3$, 0.2 g/l KBr, and 0.06 g/l $H_3BO_3$; Solution B, 21.6 g/l $MgCl_2.6H_2O$, 3.0 g/l $CaCl_2.2H_2O$, 0.05 g/l $SrCl_2.6H_2O$; Solution C, 12.5 g/l $NH_4Cl$, 7.0 g/l $K_2HPO_4$, and 50.0 g/l $CH_3CO_2Na$. Equal volumes of solutions A and B were mixed while stirring, the yeast extract and tryptone were added, and the resultant solution was sterilized by autoclaving. Solution C was sterilized separately, and 20 ml was added aseptically to 980 ml of the above mixture after cooling. Anaerobic conditions were achieved by flushing the medium with prepurified $N_2$ (Linde Gases, Baltimore, Md.) and adding 0.5 g/l $Na_2S$ (after autoclaving). Resazuring (1.0 mg/l) was used as a redox indicator. The final pH of the medium after sulfide addition was approximately 6.8.

For continuous culture, the culture vessel was a 5-neck round bottom flask (Lab. Glass Inc., Vineland, N.J.) with a total volume of 2 liters. A gas inlet tube was used to sparge the vessel, and the gas stream exiting the reactor was passed through a Graham condenser to reduce water losses, and then through a gas washing bottle containing 3.0N NaOH to remove $H_2S$. Samples for gas analysis were taken through a rubber septum mounted on the condenser outlet. The temperature in the culture vessel was maintained at 98° C. using a heating mantle, proportional temperature controller, and a type J thermocouple (Cole-Parmer Instrument Co., Chicago, Ill.). Although *P. furiosus* grows optimally at 100° C., operation slightly below this optimum prevents boiling, while supporting growth rates close to the maximum.

Medium for continuous culture experiments was added aseptically to sterile polycarbonate or polypropylene carboys (Nalge Co., Rochester, N.Y.) and maintaining under anaerobic conditions by purging with prepurified $N_2$ that was filtered through a 0.2 $\mu m$ filter (Gelman Sciences, Ann Arbor, Mich.). This culture medium was added to the reactor using a Masterflex peristaltic pump (Cole-Parmer) with a size 14 pump head. A constant reactor volume was maintained using a dip tube and a size 16 pump head connected in parallel with the inlet pump. Teflon PFA tubing (Cole-Parmer) was used between the feed reservoir and the reactor, except for a short section of silicone tubing in the pump head itself. Inlet tubing was autoclaved and aseptically connected to the medium reservoir and the reactor using Luer Lock fittings (Popper & Sons, New Hyde Park, N.Y.). A miniature double-junction pH electrode (pHoenix Electrodes, Houston, Tex.) and a Chemcadet pH controller (Cole-Parmer) were used to monitor pH in the reactor. Teflon thermometer adapters with Viton O-rings (Cole-Parmer) were used to hold the thermocouple, inlet and outlet tubes, and pH probe in the 24/40 joints of the culture flask.

Reactor inocula were grown in sealed 125 ml serum bottles containing 50 ml of the above medium along with 10 g/l elemental sulfur. These bottles were maintained under quiescent conditions at 98° C. in a temperature bath (New Brunswick Scientific Co., Inc., New Brunswick, N.J.) modified for high temperature operation and containing silicone fluid (Dow Corning Corp., Midland, Mich.). Approximately 10 ml of a late log phase culture (about 8 hours old) was used to inoculate the reactor, which contained 750 ml of medium and 10 g/l elemental sulfur. The reactor was purged with prepurified $N_2$ at a rate of 50 ml/min to ensure anaerobic conditions and mix the vessel contents (no additional agitation was supplied). Continuous operation was initiated during late log phase, and the working volume of the reactor was maintained at 750 ml. Feed rate changes were made in the direction of increasing dilution rate, and minimum of three reactor volume changes were allowed after each adjustment for the system to reach steady state. An additional 2.0 grams of sulfur were added to the reactor after every other dilution rate increase to ensure that an excess of sulfur was always present. In general, the sulfur remained in the reactor and little, if any, was carried out in the effluent.

Bacterial growth was followed by direct cell counts using epifluorescence microscopy with acridine orange stain. The production of $H_2S$ and $CO_2$ was measured using a Varian 3700 gas chromatograph (VarianAssoc., Sunnyvale, Calif.) with a 6 foot by ⅛ inch HayeSep-N column (Alltech Assoc., Deerfield, Ill.) and a thermal conductivity detector. The production of $H_2$ could not be qualified, due to interference from the $N_2$ purge. A Standard 286/10 microcomputer (CompuAdd Corp., Houston, Tex.) with a DAS-16 A/D interface (Metrabyte Corp., Taunton, Mass.) was used for data acquisition and peak integration.

The cell density/dilution rate profile for a continuous culture experiment involving *P. furiosus* was determined in the range of dilution rates from about 0.06 to 1.2 $h^{-1}$ (where a dilution rate of 1.0 $h-1$ corresponds to a flow of a volume of medium equivalent to the volume of the culture in the vessel.) Over this range of dilution rates, the pH in the reactor was between 6.4–6.8. If the growth limiting substrate is an energy source, the decrease in cell density at the lowest dilution rate tested (0.06 $h^{-1}$) could be an indication of a significant maintenance energy requirement. As the dilution rate is increased the cell density increases, reaching a maximum of about $1.6 \times 10^8$ cells/ml. This maximum cell density approaches those typically seen in batch experiments, and is maintained up to a dilution rate of about $0.8$ $h^{-1}$, gradually declining as the dilution rate is increased further.

The specific production rates of $H_2S$ and $CO_2$ from this experiment were determined based only on gas phase analysis, and as such they should be considered as minimum values. However, under these conditions ($N_2$ purge, 98° C.) the distribution of $H_2S$ and $CO_2$ is shifted strongly towards the gas phase. Therefore, rates based on gas phase analysis should be a fairly accurate measure of the true gas production rates. No correction has been made for abiotic production of either gas, but results from of the present inventors have indicated that abiotic production rates under similar conditions are typically several orders of magnitude lower than those reported here. The specific production rates of both gases are seen to increase approximately linearly as the dilution rate is increased from $0.1$ $h^{-1}$ to about $0.6$ $h^{-1}$. Above this range the relationship between specific gas production rate and dilution rate becomes non-linear, particular where $H_2S$ is concerned. SDS-PAGE of cell extracts taken at various dilution rates did not reveal any profound differences in the protein profiles of cells growing at differing rates.

Interpretation of the above results, especially the gas production data, is contingent on a clearer understanding of the metabolism of *P. furiosus*. In particular, identification of the growth limiting substrate has not yet been accomplished. The most significant result from this early work is that cell densities approaching batch maxima can be achieved at relatively high dilution rates. Considering that these maximal cell densities are low in comparison with most mesophiles, it is apparent that the most efficient strategy for generating large amounts of *P. furiosus* biomass for production of enzymes will involve operating relatively small continuous reactors at high volumetric efficiencies.

EXAMPLE 2

Proteolytic Enzyme Preparation Consisting of a Soluble Extract of *P. furiosus*

*P. furiosus* was grown on a complex medium in artificial sea water supplemented with 0.1% yeast extract, 0.5% tryptone, and 10 g/l elemental sulphur as described in Example 1. In this case, cells were grown at 98° C. in a high temperature fermentor (Bioengineering AG, Wald, Switzerland) in four or eight liter batch runs, using continuous sparging with nitrogen gas at 200 ml/min to maintain anaerobic conditions and agitated at 100 rpm with a marine impeller. Cell pellets were collected by centrifugation at low speed according to standard methods well known in the art of microbiology. Cell-free extracts were prepared by sonicating the cells for a total of three minutes with pulses at 30 sec intervals at a 50% duty cycle in a Tekmar Sonic Disrupter Model 300, and centrifuging at $25,000 \times g$ to remove cell debris.

Determination of proteolytic activity was based on the cleavage of azocasein (Cowan, D. A., et al., 1987, Biochem, J. 247:121-133). Assay mixtures contained 900 µl of 0.1% azocasein in 0.05M sodium phosphate buffer (pH 7.3 at 100° C.), and 100 µl of sample. The reaction was terminated by the addition of 500 µl of 15% (w/v) trichloracetic acid, and the cooled on ice for 5 min. The precipitate formed was removed by centrifugation at $12,000 \times g$ for 3 min in a microcentrifuge. Color release as a result of proteolytic activity was detected by measuring the absorbance of the supernatant at 440 nm. Linear response of the assay was obtained between 0.010 and 0.100 absorbance units. A unit of activity is defined as the amount of protein which produces a change of 0.100 absorbance units at 440 nm for a 30 min. incubation at a given temperature. Total protein was measured using the BioRad assay kit.

After conventional SDS-PAGE separation, proteolytic activity of protein bands was determined by overlaying the first gel with a 10% polyacrylamide gel contain 1% SDS and 0.5% gelatin (Hare, P., et al., 1983, J. Gen. Microbiol. 129:1141-1147). The gels were pressed together to remove air bubbles and kept moist with 50 mM sodium phosphate (pH 7.5) buffer during the transfer. The Transfer step was performed at 75° C. for five hours. The gelatin gel was then removed, cooled to 4° C., and stained with a solution of 1.8 g/l amido black and 0.04 g/l Coomassie Blue. Proteolytic activity was evidenced by white bands resulting from the gelatin cleavage in the stained gel. Molecular weight markers (MW) from the gel without gelatin were stained with Coomassie blue-amido black staining solution (0.04 g/l amido black and 2 g/l Coomassie blue in 35% methanol and 7% acetic acid) for 30 min and then destained overnight in 35% methanol and 7% acetic acid.

EXAMPLE 3

Purified Proteolytic Enzyme Preparation from *Pyrococcus furiosus*.

Purified samples of the SDS-resistant protease were obtained by incubation of the cell-free extract for 24 hours in the presence of 1% SDS at 98° C. Extracts treated in this way were then dialyzed against 5 mM sodium phosphate buffer, pH 7.5 at 4° C. overnight and concentrated in a Pharmacia Omegacell Stirred Cell (nominal molecular weight limit of 10 kDa) to a concentration of 2-3 mg/ml protein measured by the Bio-Rad protein assay kit.

For tests on the substrate specificity of the purified SDS-resistant preparation, benzoyl-L-arginine ethyl ester, benzoyl-DL-arginine p-nitroanilide, serum thymic factor, angiotensin I, and trypsin were obtained from Sigma. Assays of benzoyl-L-arginine ethyl ester and benzoyl-arginine p-nitroanilide were performed as described previously (Schwert, G. W. et al., 1955, Biochem. Biophys. Acta 16:570-575; Erlanger, B. F., et al., 1961, Arch. Biochem. Biophys. 95:271-278) with a change in buffers to 50 mM sodium phosphate buffer, pH 7.5, and a substrate preincubation of two minutes at standard assay temperature.

Hydrolysis of peptides was conducted with a modification of a procedure described by Cowan et al., 1987, Biochem. J. 247:121-133). The peptides serum thymic factor and angiotensin I were incubated with the protease from *P. furiosus* for fifteen and sixty minutes at 98° C., and two hours with trypsin at 40° C. End products were separated by reverse phase chromatography on a Waters high-performance liquid chromatography system using a WISP auto injector and µ-Bondapak $C_{18}$ with a linear gradient of acetonitrile and water, with 0.1% trifluoroacetic acid in both phases. Peaks from the reverse phase column were dried down in a Savant Speed-Vac and analyzed by Waters Pico-Tag amino acid analysis.

For purposes of completing the background description and present disclosure, each of the published articles, patents and patent applications heretofore identified in this specification are hereby incorporated by reference into the specification.

The foregoing invention has been described in some detail for purposes of clarity and understanding. It will be obvious to one of ordinary skill in the art that various combinations in form and detail can be made without departing from the scope of this invention.

What is claimed is:

1. A purified proteolytic enzyme preparation obtained from *Pyrococcus furiosus* comprising the steps of cultivating *Pyrococcus furiosus* in nutrient medium suitable for *Pyrococcus furiosus* growth, disrupting said *Pyrococcus furiosus* to obtain a cell extract, and maintaining the resulting cell extract at about 100° C. for a time period in the range of from about 1 hour to about 105 hours.

2. The purified proteolytic enzyme preparation according to claim 1 wherein said *Pyrococcus furiosus* is the deposit DSM 3638 of the Deutsche Sammlung von Mikroorganism, Federal Republic of Germany.

3. The purified proteolytic enzyme preparation according to claim 1 further having a pH optimum at 98° C. for proteolytic activity of about 6.8, and having a half-maximal activity over the range of about pH 4.5 to pH 9.3 during 30 minute assays, and further retaining about 2% of original activity after incubation at about pH 9.3 for 3 hours.

4. The purified proteolytic enzyme preparation according to claim 1, further having resistance to inactivation by either 1 molar urea or 1 molar guanidinium chloride with no loss of proteolytic activity at 98° C. for at least 30 minutes.

5. The purified proteolytic enzyme preparation according to claim 1 further having a half-life of proteolytic activity at 98° C. of about 60 hours wherein said preparation includes five proteolytic enzyme species having approximate molecular mass values in kilodaltons of: 140; 125; 116; 102 and 66, determined by SDS-PAGE.

6. The proteolytic enzyme preparation according to claim 1 further having a half-life of proteolytic activity at 98° C. of about 12 hours in the presence of sodium dodecyl sulfate at a concentration of about 1% by weight per volume.

7. A purified proteolytic enzyme preparation obtained from a hyperthermophilic bacterium comprising the steps of cultivating hyperthermophilic bacterium in nutrient medium suitable for hyperthermophilic bacterium growth, disrupting said bacterium to provide a cell extract by optionally adding sodium dodecyl sulfate at a concentration of about 1%, incubating said cell extract at about 100° C. for a period of time in the range of about 1 hour to about 24 hours, such that a purified proteolytic enzyme preparation is obtained; said proteolytic enzyme having a half-life of proteolytic activity of about 12 hours in the presence of sodium dodecyl sulfate at a concentration of about 1% by weight per volume.

8. The purified proteolytic enzyme preparation according to claim 7 wherein said hyperthermophilic bacterium is *Pyrococcus furiosus*.

* * * * *